United States Patent
Choi et al.

(10) Patent No.: US 11,419,708 B2
(45) Date of Patent: Aug. 23, 2022

(54) DIGITAL DENTURE MANUFACTURING METHOD AND MANUFACTURING SYSTEM, AND DENTURE HOLE GUIDER APPLIED THERETO AND MANUFACTURING METHOD THEREOF

(71) Applicant: DIO Corporation, Busan (KR)

(72) Inventors: Byung Ho Choi, Wonju-si (KR); Seung Mi Jung, Wonju-si (KR); Jin Cheol Kim, Yangsan-si (KR); Jin Baek Kim, Busan (KR)

(73) Assignee: DIO CORPORATION, Busan (KR)

( * ) Notice: Subject to any disclaimer, the term of this patent is extended or adjusted under 35 U.S.C. 154(b) by 151 days.

(21) Appl. No.: 16/628,072

(22) PCT Filed: Feb. 23, 2018

(86) PCT No.: PCT/KR2018/002225
§ 371 (c)(1),
(2) Date: Jan. 2, 2020

(87) PCT Pub. No.: WO2019/009494
PCT Pub. Date: Jan. 10, 2019

(65) Prior Publication Data
US 2021/0153985 A1 May 27, 2021

(30) Foreign Application Priority Data

Jul. 7, 2017 (KR) .................. 10-2017-0086457
Jul. 21, 2017 (KR) .................. 10-2017-0092588
Aug. 28, 2017 (KR) .................. 10-2017-0108558

(51) Int. Cl.
*G06T 15/00* (2011.01)
*A61C 13/00* (2006.01)
(Continued)

(52) U.S. Cl.
CPC .......... *A61C 13/0004* (2013.01); *A61C 1/084* (2013.01); *A61C 9/0046* (2013.01);
(Continued)

(58) Field of Classification Search
None
See application file for complete search history.

(56) References Cited

U.S. PATENT DOCUMENTS 9,642,678 B2 * 5/2017 Kuo .................. A61C 7/08
2007/0190492 A1 8/2007 Schmitt
(Continued)

FOREIGN PATENT DOCUMENTS

JP 2010521237 6/2010
JP 5237106 7/2013
(Continued)

OTHER PUBLICATIONS

Chang et al., Digital Denture Manufacturing—An Integrated Technologies of Abrasive Computer Tomography, CNC Machining and Rapid Prototyping, 2006, The International Journal of Advanced Manufacturing Technology, 31:41-49 (Year: 2006).*
(Continued)

*Primary Examiner* — Anh-Tuan V Nguyen (74) *Attorney, Agent, or Firm* — Lex IP Meister, PLLC (57) ABSTRACT

In order to improve manufacturing convenience and precision, the present invention provides a digital denture manufacturing method comprising: a first step of acquiring a three-dimensional work image, on which occlusion information between a target dental arch and an opposing dental
(Continued)

arch and implant information of a fixture implanted in the target dental arch are displayed, and preparing a temporary denture in which a binding region formed to correspond to a binding portion profile of an abutment fastened to the fixture is arrayed and arranged; a second step of acquiring an auxiliary scan image for the temporary denture; a third step of acquiring, from the auxiliary scan image, a correction surface image on three-dimensional surface information of an inner surface-side engagement groove of the temporary denture including the binding region; and a fourth step of designing and manufacturing a digital denture having a virtual binding groove corresponding to the position and the shape of the three-dimensional surface information of the binding region, in an inner surface profile set according to the three-dimensional surface information of the engagement groove.

7 Claims, 5 Drawing Sheets

(51) Int. Cl.
*G16H 30/40* (2018.01)
*A61C 1/08* (2006.01)
*A61C 9/00* (2006.01)
*A61C 13/107* (2006.01)
*G06T 19/20* (2011.01)

(52) U.S. Cl.
CPC ......... *A61C 13/0001* (2013.01); *G16H 30/40* (2018.01); *G06T 19/20* (2013.01)

(56) References Cited

U.S. PATENT DOCUMENTS

| | | | |
|---|---|---|---|
| 2009/0042167 A1* | 2/2009 | Van Der Zel | A61C 9/0053 433/172 |
| 2009/0111071 A1* | 4/2009 | Yau | A61C 8/005 433/173 |
| 2014/0255873 A1 | 9/2014 | Bullis et al. | |
| 2014/0272779 A1* | 9/2014 | Okay | A61C 9/0053 433/173 |
| 2015/0025855 A1* | 1/2015 | Fisker | A61C 1/082 703/1 |
| 2015/0230894 A1 | 8/2015 | Juzbasic et al. | |
| 2015/0282904 A1* | 10/2015 | Fisker | G05B 19/4097 700/98 |
| 2015/0359615 A1* | 12/2015 | Sabina | A61C 13/0004 264/16 |
| 2016/0135931 A1 | 5/2016 | Morales et al. | |
| 2016/0157967 A1* | 6/2016 | Kim | A61C 13/26 433/201.1 |

FOREIGN PATENT DOCUMENTS

| | | |
|---|---|---|
| WO | 2009027316 | 3/2009 |
| WO | 2012041329 | 4/2012 |
| WO | 2014056104 | 4/2014 |

OTHER PUBLICATIONS

KIPO, International Search Report of PCT/KR2018/002225 dated Jun. 27, 2018.

* cited by examiner

though a process of injecting a resin between the binding hole and the support cylinder and curing the resin, the binding hole is coupled to the support cylinder so that an initial installation process of the denture is completed. As such, the installation process of the denture becomes quite complicated, and the cured resin has a weak support force for a body of the denture and is easily separated, and thus the installation stability and durability of the denture are lowered.

In order to reduce such a limitation, a method of manufacturing a denture by fastening an impressing coping and the like to the fixture and then acquiring an impression on a target dental arch has been used. That is, a model of a target dental arch is formed using an inner surface profile of the acquired impression, and the position and angle of the binding hole are set on the basis of the impression coping so that the denture is manufactured.

However, the impression acquisition method described above causes discomfort to a denture subject due to a foreign material sensation when the impression is being acquired. In addition, the burden of the operator is increased due to a large number of process steps being complicated and having a high level of difficulty, and errors of each process step are often accumulated, which causes a degradation of precision.

DIGITAL DENTURE MANUFACTURING METHOD AND MANUFACTURING SYSTEM, AND DENTURE HOLE GUIDER APPLIED THERETO AND MANUFACTURING METHOD THEREOF

TECHNICAL FIELD

The present invention relates to a digital denture manufacturing method and manufacturing system, a denture hole guider applied to the manufacturing method and manufacturing system, and a manufacturing method of the denture hole guider, and more specifically, to a digital denture manufacturing method and manufacturing system, a denture hole guider applied to the manufacturing method and manufacturing system, and a manufacturing method of the denture hole guider, which ensure an improved manufacturing convenience and precision.

BACKGROUND ART

Generally, false teeth or dentures refer to intraoral artificial periodontium that artificially restore an appearance and functions by replacing missing natural teeth. Such false teeth or dentures may be installed inside the oral cavity to restore a mastication function and prevent deformation of periodontium and may be divided into partial/complete false teeth and partial/complete dentures according to the number of missing teeth.

Here, the false teeth may be bonded to and installed on the surface of the gum by a dental adhesive applied to an inner surface-side engagement groove thereof, and the denture may be installed in the oral cavity through a fixture implanted in the alveolar bone. In this case, the false teeth, which are supported by the gum, cause deformation of the gum or a great deal of foreign material sensation, and thus use of the dentures supported by the alveolar bone is increasing.

Meanwhile, the denture is formed with a binding hole to which a support cylinder is fixed.

In detail, when a perforation is formed in the alveolar bone and a fixture is implanted into the perforation and an abutment is installed on the fixture, the support cylinder is coupled to the abutment so that the denture is installed inside the oral cavity. In this case, the fixture/abutment and the support cylinder are provided in a plural of units thereof according to the size of the denture, and each support cylinder is coupled to one fixture/abutment in one-to-one correspondence so that the denture may be stably installed.

However, since the conventional technology uses a method of predicting an installation position of a previously manufactured denture in the oral cavity and an implant position of the fixture/abutment, machining a binding hole in the denture, and fixing the support cylinder, the binding hole varies significantly in position.

In detail, according to the conventional technology, the support cylinder is fastened to the fixture/abutment implanted and installed in the alveolar bone, and then a denture primarily formed with a binding hole having a wide size in consideration of manufacturing errors is positioned inside the oral cavity. Then, the binding hole expands according to a positional deviation with respect to the support cylinder, and when the machining of the binding hole is completed to a size by which the support cylinder is completely insertable into the binding hole, the denture is temporarily fixed to a predetermined installation position.

DISCLOSURE

Technical Problem

The present invention is directed to providing a digital denture manufacturing method and manufacturing system, a denture hole guider applied to the digital denture manufacturing method and manufacturing system, and a manufacturing method of the denture hole guider, which may improve the manufacturing convenience and precision.

Technical Solution

One aspect of the present invention provides a digital denture manufacturing method including the steps of: a first step of acquiring a three-dimensional (3D) work image, on which occlusion information between a target dental arch and an opposing dental arch and implant information of a fixture implanted in the target dental arch are displayed, and preparing a temporary denture in which a binding region formed to correspond to a binding portion profile of an abutment fastened to the fixture is arranged; a second step of acquiring an auxiliary scan image for the temporary denture; a third step of acquiring, from the auxiliary scan image, a correction surface image on 3D surface information of an inner surface-side engagement groove of the temporary denture including the binding region; and a fourth step of designing and manufacturing a digital denture having a virtual binding groove corresponding to a position and shape of the 3D surface information of the binding region in an inner surface profile set according to the 3D surface information of the engagement groove.

Another aspect of the present invention provides a digital denture manufacturing system including: an imaging apparatus configured to acquire an auxiliary scan image for a temporary denture in which a binding region formed to correspond to an abutment fastened to a fixture implanted in a target dental arch is arranged; a planning unit configured to acquire, from the auxiliary scan image, a correction surface image on three-dimensional (3D) surface information of an inner surface-side engagement groove of the temporary denture including the binding region, set an inner surface profile according to the 3D surface information of the engagement groove, and set a virtual binding groove corresponding to a position and shape of the 3D surface information of the binding region in the inner surface profile so that a digital denture is designed; and a manufacturing apparatus configured to manufacture the designed digital denture.

Another aspect of the present invention provides a method of manufacturing a denture hole guider for forming a binding hole, in which a support cylinder is installed, in false teeth mounted on a target dental arch, the method including the steps of: a first step of acquiring a three-dimensional (3D) work image on which implant information of a fixture implanted in the target dental arch and a false teeth image corresponding to the false teeth are displayed; a second step of setting a virtual binding hole to correspond to the implant information of the fixture; and a third step of setting an outer surface profile according to three-dimensional surface information of an inner surface-side engagement groove of the false teeth image and setting a virtual alignment hole overlapping an extension region of the virtual binding hole so that the denture hole guider is designed and manufactured.

Another aspect of the present invention provides a denture hole guider including: an opposing engagement portion, which forms a binding hole in which a support cylinder is installed in false teeth mounted on a target dental arch, provided on one surface with a protrusion protruding to correspond to three-dimensional (3D) surface information of an engagement groove of the false teeth such that the opposing engagement portion is inserted into the engagement groove; and an alignment hole formed to pass through the opposing engagement portion to guide a drilling position and a drilling angle of the binding hole and set to be arranged to overlap an extension region of a virtual binding hole set according to implant information of a fixture displayed on a 3D work image.

Advantageous Effects

Through the above solution, the present invention provides the following effects.

First, unlike the conventional technology of acquiring an impression on a target dental arch, a digital denture can be designed and manufactured in a simple and high-precision manner using a three-dimensional (3D) work image. In addition, design information of the digital denture acquired by 3D vector data can be easily stored and managed, and remanufacturing is easily performed when the denture is damaged or lost so that the manufacturing convenience can be improved.

Second, a surface profile of a target dental arch and implant information of a fixture are replaced and corrected with images acquired for a temporary denture and a support cylinder installed in the temporary denture. Accordingly, a high-precision image, which minimizes variations due to vibration/shaking/distortion generated in a process of acquiring an intraoral image, is used in a process of designing an engagement groove and a binding groove of a digital denture so that the accuracy can be improved.

Third, design information precisely corresponding to a target dental arch and a binding region is clearly exposed and acquired using a simple method of deleting unnecessary image parts from 3D surface information acquired by scanning a temporary denture. Accordingly, the digital denture designed and manufactured on the basis of the design information can be provided with significantly improved precision.

Fourth, a previously used adhesive type denture can be easily converted and processed into a temporary denture that can be installed in a target dental arch through a fixture and a support cylinder using a denture hole guider. In addition, a binding hole formed in the denture hole guider is set to precisely correspond to the position of the fixture/support cylinder so that precision processing of the binding hole can be achieved.

BEST MODES OF THE INVENTION

Hereinafter, example embodiments of the present invention will be described with reference to the accompanying drawings in detail.

MODES OF THE INVENTION

Hereinafter, a digital denture manufacturing method and manufacturing system, a denture hole guider applied to the manufacturing method and manufacturing system, and a manufacturing method of the denture hole guider according to embodiments of the present invention will be described with reference to the accompanying drawings.

Figure 1:
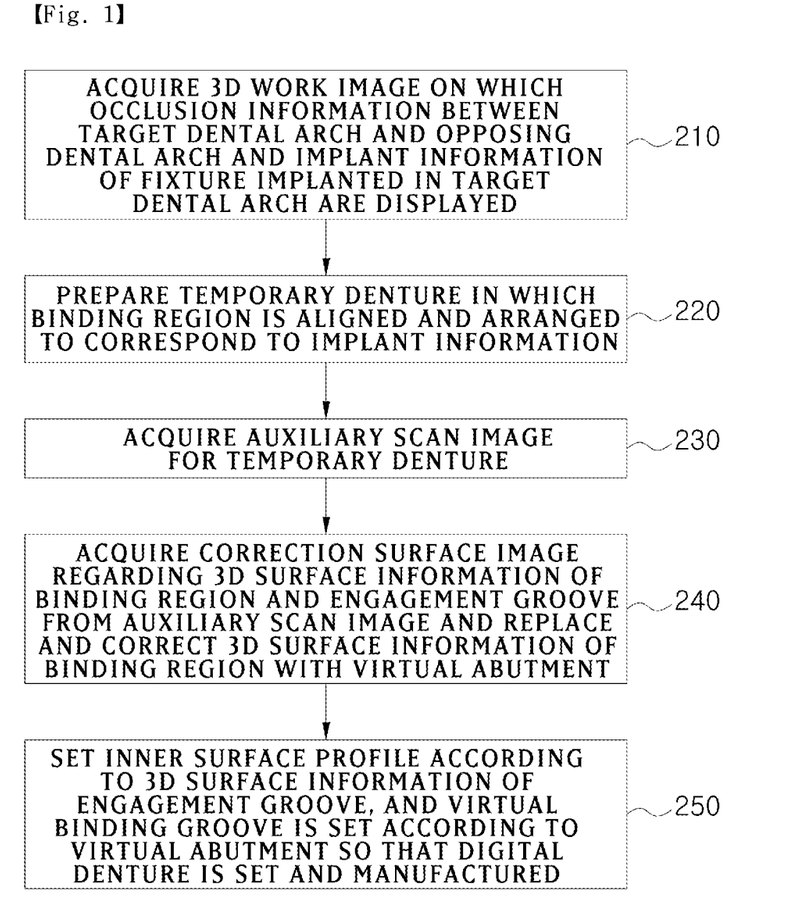
FIG. 1 is a flowchart showing a digital denture manufacturing method according to an embodiment of the present invention.
Figure 2:
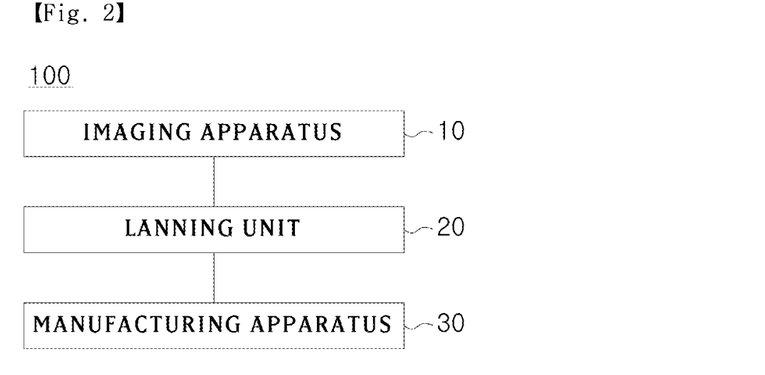
FIG. 2 is a block diagram illustrating a digital denture manufacturing system according to an embodiment of the present invention.

FIG. 1 is a flowchart showing a digital denture manufacturing method according to an embodiment of the present invention, and FIG. 2 is a block diagram illustrating a digital denture manufacturing system according to an embodiment of the present invention.

Referring to FIGS. 1 to 2, the digital denture manufacturing method according to the present invention includes acquiring a three-dimensional (3D) work image (210), preparing a temporary denture (220), acquiring an auxiliary scan image (230), acquiring a correction surface image on the basis of the auxiliary scan image (240), and designing and manufacturing a digital denture using the correction surface image (250).

On the other hand, the present embodiment describes and illustrates an example of a process of manufacturing a complete denture which is installed inside an oral cavity where a side of either an upper jaw or a lower jaw is edentulous or both the upper jaw and the lower jaw are edentulous. However, the digital denture manufacturing method according to the present invention may be applied to a partial denture manufacturing process in the same manner.

In addition, the digital denture manufacturing method according to the present invention may be performed using a digital denture system 100 including an imaging apparatus 10, a planning unit 20, and a manufacturing apparatus 30. In this case, it should be understood that the imaging apparatus 10 is a concept encompassing an intraoral scanner and a computed tomography (CT) imaging apparatus. A denture hole guider manufacturing method described below may also be performed using the digital denture manufacturing system 100.

Figure 3:
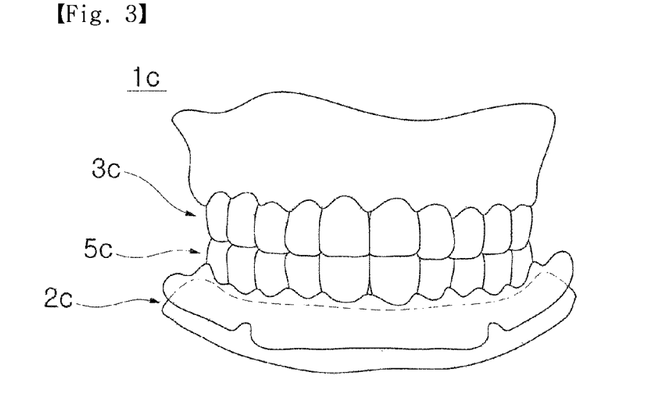
FIG. 3 is an exemplary diagram illustrating a base occlusion image in a digital denture manufacturing method according to an embodiment of the present invention.
Figure 4:
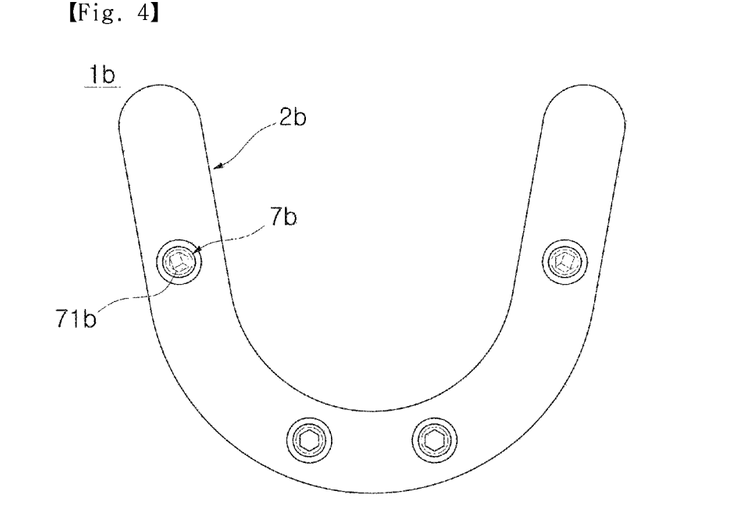
FIG. 4 is an exemplary diagram illustrating a surface image in a digital denture manufacturing method according to an embodiment of the present invention.
Figure 5:
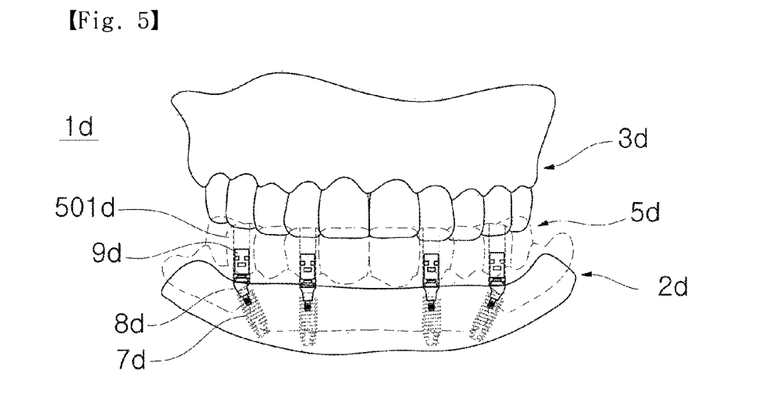
FIG. 5 is an exemplary diagram illustrating a process of designing a binding hole in a digital denture manufacturing method according to an embodiment of the present invention.
Figure 6:
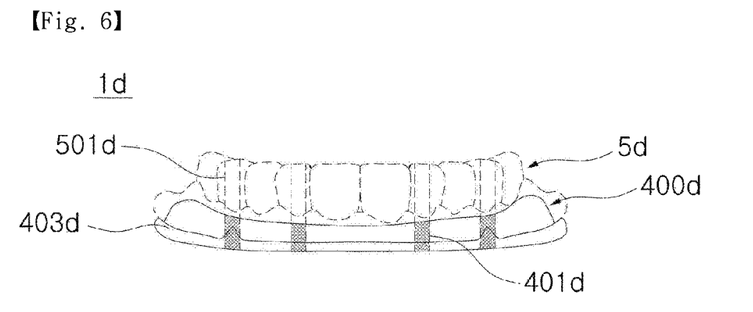
FIG. 6 is an exemplary diagram illustrating a process of designing a denture hole guider in a digital denture manufacturing method according to an embodiment of the present invention.
Figure 7A:
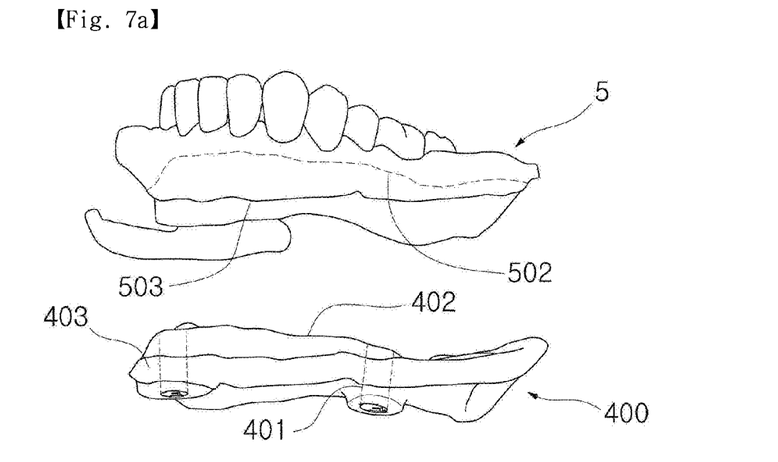
FIGS. 7A and 7B are exemplary diagrams illustrating a binding hole drilling process using a denture hole guider manufactured by a digital denture manufacturing method according to an embodiment of the present invention.
Figure 7B:
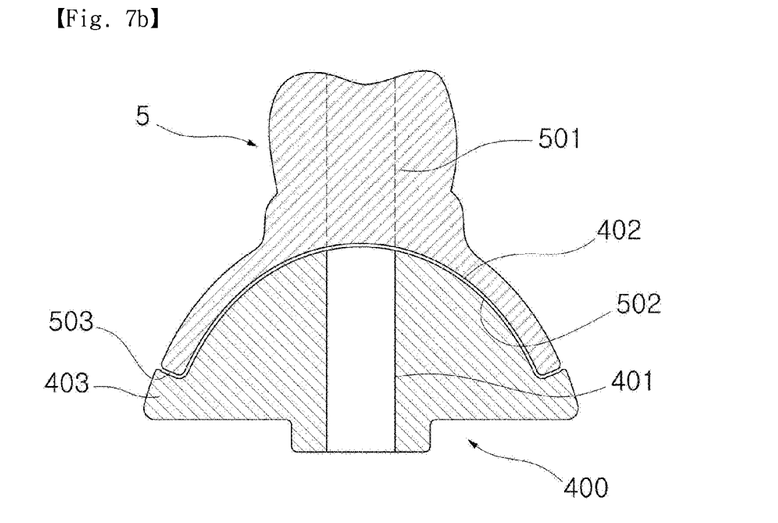

FIG. 3 is an exemplary diagram illustrating a base occlusion image in a digital denture manufacturing method according to an embodiment of the present invention, FIG. 4 is an exemplary diagram illustrating a surface image in a digital denture manufacturing method according to an embodiment of the present invention, FIG. 5 is an exemplary diagram illustrating a process of designing a binding hole in a digital denture manufacturing method according to an embodiment of the present invention, FIG. 6 is an exemplary diagram illustrating a process of designing a denture hole guider in a digital denture manufacturing method according to an embodiment of the present invention, and FIGS. 7A and 7B are exemplary diagrams illustrating a binding hole drilling process using a denture hole guider manufactured by a digital denture manufacturing method according to an embodiment of the present invention.

As shown in FIGS. 3 to 7B, first, a 3D work image 1d, on which occlusion information between a target dental arch and an opposing dental arch and implant information of a fixture implanted in the target dental arch are displayed, is acquired (210 in FIG. 1).

Here, the target dental arch refers to a dental arch that requires a denture treatment, and the following description will be made in relation to the fact that an example of the target dental arch is a lower jaw. In addition, it should be understood that the opposing dental arch is a dental arch that opposes the target dental arch.

In addition, the occlusion information refers to an occlusal vertical dimension between the target dental arch and the opposing dental arch that provides a suitable mastication sensation to a denture subject. In addition, the implant information of the fixture refers to information indicating the position and the implant angle of the fixture previously implanted or to be implanted in the target dental arch. In addition, the implant information of the fixture should be understood as including information about the shape, position, and angle of an abutment fastened to the fixture.

In this case, the implant information of the fixture may be acquired on the basis of a fixture image displayed in the 3D work image 1d when an actual fixture has been previously implanted in the target dental arch. Alternatively, when the fixture has not been implanted in the target dental arch, the implant information of the fixture may be acquired on the basis of a virtual fixture 7d that is virtually disposed on the basis of periodontium information displayed in the 3D work image 1d.

In addition, the 3D work image 1d should be understood as image data representing periodontium information, such as gums, teeth, and alveolar bones, of the target dental arch and the opposing dental arch. The 3D work image 1d may be acquired through the intraoral scanner or the CT imaging apparatus or may be acquired by registering or matching two or more pieces of image data.

Meanwhile, the 3D work image 1d may be acquired by matching a surface image 1b with a base occlusion image 1c. Here, the base occlusion image 1c refers to an image of the false teeth mounted on the target dental arch that is acquired through the intraoral scanner in an occlusion state of the false teeth and the opposing dental arch.

In this case, the term "false teeth" may be false teeth previously used by the denture subject and refers to artificial periodontium adhesively fixed with a dental adhesive without using a fixture, an abutment, a support cylinder, and the like. In addition, a temporary denture or a digital denture described below refers to artificial periodontium installed in the target dental arch through the fixture, the abutment, the support cylinder, and the like.

In detail, referring to FIG. 3, on the base occlusion image 1c, a false teeth image 5c representing surface shape information of the false teeth and a target dental arch image 2c representing partial surface shape information of a target dental arch on which the false teeth are mounted are displayed. In addition, an opposing dental arch image representing surface shape information of the gum, teeth, and the like of an opposing dental arch is displayed.

In this case, the base occlusion image 1c is acquired in a state in which the opposing dental arch having an implant or residual tooth is occluded with the false teeth mounted on the target dental arch. Accordingly, the false teeth image 5c of false teeth pressed against the target dental arch may be displayed together with the occlusal vertical dimension suitable for the denture subject.

When false teeth are not being used, an occlusion alignment base coated with an impression material is disposed between the target dental arch and the opposing dental arch, and the thickness of the occlusion alignment base is adjusted according to the mastication sensation of the denture subject so that the occlusal vertical dimension is calculated. In addition, a process of manufacturing false teeth having an artificial gum portion and an artificial teeth portion by reflecting an impression profile of the impression material and the calculated occlusal vertical dimension may be performed. Here, an engagement groove to be engaged with the surface of the target dental arch is formed in the artificial gum portion through the impression material. The artificial teeth portion may be formed at a height corresponding to a mastication region of the opposing dental arch from the surface of the artificial gum portion on the basis of the occlusion information.

In addition, referring to FIG. 4, the surface image 1b may be acquired by imaging the target dental arch in which the false teeth has been removed with the intraoral scanner. Accordingly, the surface image 1b may display a target dental arch image 2b representing surface shape information of the gum of the target dental arch having been covered by the false teeth. The surface image 1b may be displayed on the basis of 3D surface information of an inner surface-side engagement groove profile of the false teeth or on the basis of an inner surface-side engagement groove profile of the false teeth that is inverted and represented in 3D.

In this case, when the fixture is previously implanted in the target dental arch, a fixture image 7b representing shape information of one end side of the fixture may be displayed on the surface image 1b. In detail, a polygonal fastening groove for fastening with the abutment is formed in the one end of the fixture, and a fastening groove image 71b corresponding to the surface shape of the fastening groove is displayed on the fixture image 7b.

On the other hand, the surface image 1b and the base occlusion image 1c may be acquired through the imaging apparatus 10 (see FIG. 2) provided on an operator side such as a dental office and may be transmitted to a manufacturer side server, such as a medical procedure support center. The surface image 1b and the base occlusion image 1c transmitted to the manufacturer side server may be matched with each other through the planning unit 20 (see FIG. 2) to be acquired as a 3D work image 1d. Here, the surface image 1b and the base occlusion image 1c may be matched with each other through a common portion, such as the gum surface exposed to the outside of the false teeth, or using a marker or the like installed on the gum surface of the target dental arch.

In this case, a series of design processes of a denture hole guider or digital denture, which will be described below, may be performed on the basis of the 3D work image 1d through the planning unit 20 (see FIG. 2). In detail, the planning unit 20 (see FIG. 2) may be provided as a personal computer (PC) that is connected to the manufacturer side server and performs arithmetic processing for each image. In addition, the 3D work image 1d may be acquired through the planning unit 20 (see FIG. 2), and each process operation, such as the designing of the denture hole guider or the designing of the digital denture, may be performed or supported on the basis of the 3D work image 1d.

Meanwhile, referring to FIG. 5, on the 3D work image 1d, gum surface shape information of the target dental arch covered by the false teeth is replaced with the target dental arch image 2b (see FIG. 4) included in the surface image 1b (see FIG. 4) on the basis of the occlusal vertical dimension. Accordingly, on the 3D work image 1d, a basic target dental arch image 2d representing substantial surface shape information of the target dental arch is displayed. In addition, a basic opposing dental arch image 3d representing surface shape information of the opposing dental arch may be arranged to correspond to the basic target dental arch image 2d with the occlusal vertical dimension and may be displayed as occlusion information.

In addition, a basic false teeth image 5d representing surface shape information of the false teeth is displayed on the 3D work image 1d, and implant information of a fixture previously implanted in the target dental arch is displayed on the basic target dental arch image 2d. In this case, the implant information of the fixture should be understood as the fastening groove image 71b (see FIG. 4).

Alternatively, when no fixture is implanted in the target dental arch, the virtual fixture 7d may be virtually arranged on the basis of the basic false teeth image 5d in the 3D work image 1d.

Here, the virtual fixture 7d, and a virtual abutment 8d and a virtual support cylinder 9d described below refer to 3D appearance information of a physical fixture, an abutment, and a support cylinder actually implanted in the target dental arch. Furthermore, the virtual fixture 7d, the virtual abutment 8d, and the virtual support cylinder 9d should be understood as a concept of encompassing vector data corresponding to the 3D appearance information and 3D images corresponding to the vector data. The 3D appearance information may be directly acquired by scanning or CT imaging the physical fixture, abutment, and support cylinder and may be previously stored in the form of database in a storage of the planning unit 20 (see FIG. 2).

In addition, the virtual arrangement should be understood as a concept that encompasses allowing 3D appearance information corresponding to a real object to be displayed in the form of an image in the 3D work image 1d or to be calculated as 3D coordinates.

In this case, as the virtual fixture 7d is virtually arranged in the 3D work image 1d, surface shape information of the fastening groove and an implant angle that are implant information of the fixture for guiding the implant position of the fixture actually implanted in the oral cavity may be calculated.

A CT image of the target dental arch and the opposing dental arch may be further acquired in the process of acquiring the 3D work image 1d.

In detail, the CT image may be acquired through the CT imaging apparatus and may include information about internal tissues such as alveolar bone shape, density, and neural tissue. In this case, when a fixture is previously implanted in the target dental arch, the position and the implant angle of the previously implanted fixture may be further displayed.

The base occlusion image 1c, the surface image 1b, and the CT image may be matched and adjusted through the planning unit 20 (see FIG. 2) to be acquired as the 3D work image 1d. Accordingly, on the 3D work image 1d, tissue information of the alveolar bones, shape information and a nerve tissue image of the gum of the target dental arch, and tissue information of the alveolar bones and teeth and shape information of the gum of the opposing dental arch may be displayed.

In this case, when a fixture is previously implanted in the target dental arch, implant information of the fixture displayed on the CT image may be adjusted or matched with the basic target dental arch image 2d and displayed in the 3D work image 1d.

Alternatively, when a fixture has not been implanted in the target dental arch, the virtual fixture 7d may be virtually disposed at the position and angle suitable for the periodontium of the denture subject using the tissue and nerve information of the target dental arch included in the CT image. In some cases, the 3D work image 1d may be acquired by matching the CT image with the surface image 1b.

Hereinafter, the virtual fixture 7d displayed on the 3D work image 1d should be understood as including an image converted from 3D vector data and virtually disposed and image information of a fixture directly captured and displayed on the CT image.

In detail, when the 3D work image 1d is acquired (210 in FIG. 1), a virtual binding hole 501d is preliminarily set to correspond to the implant information of the fixture. Here, the virtual binding hole 501d should be understood as design information of a binding hole, which is a perforated portion actually formed in a physical temporary denture, that is, a 3D image or 3D vector data virtually disposed in the 3D work image $1d$.

In detail, the virtual binding hole $501d$ may be set as cylindrical region information corresponding to an outer diameter of the support cylinder. In addition, the virtual binding hole $501d$ may be primarily set as 3D coordinates on the basis of the implant information of the fixture and may be virtually arranged in the 3D work image $1d$.

In this case, in order for the virtual binding hole $501d$ to be disposed at a more accurate position, the virtual abutment $8d$ and the virtual support cylinder $9d$ may be virtually arranged to correspond to the implant information of the virtual fixture $7d$ in the 3D work image $1d$. The virtual binding hole $501d$ is arranged to match with an outer periphery region of the virtual support cylinder $9d$ virtually arranged in the 3D work image $1d$.

Furthermore, the basic false teeth image $5d$ included in the 3D work image $1d$ is displayed in a state in which the engagement groove is pressed exactly against the target dental arch. Accordingly, the virtual binding hole $501d$ may be precisely set by accurately reflecting the implant position of the fixture/abutment/support cylinder and the installation position of the false teeth.

Here, the support cylinder is coupled to the abutment fastened to the fixture implanted in the target dental arch while protruding from the surface of the alveolar bone or the gum of the target dental arch and is fixed to the binding hole formed in the temporary denture to support the temporary denture.

In addition, the implant number and positions of the fixtures may be set to support a mastication pressure calculated according to the number of opposing teeth occluded with the temporary denture. Then, when the implant number and positions of the fixtures are set, the implant angle of the fixture for each implant position may be set in consideration of the shape, density, neural tissue arrangement, and the like of the alveolar bone corresponding to each position.

For example, when the target dental arch is a completely edentulous lower jaw, the implant number and positions of the fixtures may be set to four places, including two for anterior teeth sides and two for molar teeth sides.

In this case, in the vicinity of the anterior teeth side alveolar bone, since a large amount of alveolar bones exist and neural tissues are not distributed, the implant angle of the anterior teeth side fixture may be set to the vertical direction. In the vicinity of one side or the other side of the molar teeth side alveolar bone, no alveolar bone exists and nerve tissues are distributed at the lower side. Accordingly, the implant angle of the molar teeth side fixture of the lower jaw may be set to an inclined direction to avoid the neural tissues while forming a strong support force.

In addition, the support cylinder is coupled to the abutment fastened to the fixture, and the abutment may be provided as a straight-type general abutment and a bent-type multi abutment such that the support cylinder is arranged toward the opposing dental arch.

That is, the straight type general abutment is fastened to the anterior teeth side fixture, and the fixture, the general abutment, and the support cylinder may be arranged in the vertical direction. In addition, the bent type multi abutment is fastened to the molar teeth side fixture. In this case, the multi-abutment may have a lower end portion bent to correspond to the inclined implant angle of the fixture but may have an upper end portion extending in the vertical direction so that the support cylinder is supported in the vertical direction.

Meanwhile, when the virtual support cylinder $9d$ is virtually disposed in the 3D work image $1d$, the virtual binding hole $501d$ may be arranged and moved according to 3D coordinates of the virtual support cylinder $9d$.

In detail, when a perforation is formed in the target dental arch, the fixture is implanted in the perforation and the abutment is fastened to the implanted fixture. The support cylinder is coupled to the fastened abutment, and as the coupled support cylinder is fixed to the binding hole, the temporary denture is installed in the target dental arch.

Alternatively, the temporary denture may be installed in the target dental arch by allowing the support cylinder, which is integrally fixed to the binding hole, to be coupled the abutment. Alternatively, the temporary denture may be installed in the target dental arch by allowing the support cylinder and the abutment, which are coupled to each other, to be fixed to the binding hole. Preferably, the support cylinder and the abutment are separately provided, but according to embodiments, the support cylinder and the abutment may be provided to be integrally connected to each other.

In this case, the virtual binding hole $501d$ is set on the basis of an overlapping region of the basic false teeth image $5d$ and the virtual support cylinder $9d$ displayed on the 3D work image $1d$ and may further include a predetermined tolerance area. That is, the virtual binding hole $501d$ may be set to extend radially outward from the overlapping region.

Furthermore, the virtual abutment $8d$ and the virtual support cylinder $9d$ are virtually disposed in the 3D work image $1d$ on the basis of the implant information of the fixture. Accordingly, the positional relationship of the fixture/abutment/support cylinder actually implanted in the target dental arch may be accurately predicted on the basis of the 3D work image $1d$ in which the virtual abutment $8d$ and the virtual support cylinder $9d$ are virtually disposed. Since the predicted positions of the fixture/abutment/support cylinder are reflected in the process of designing the virtual binding hole $501d$, the virtual binding hole $501d$ may be precisely set.

Here, in the virtual arrangement of the virtual abutment $8d$, an operation may be further included of allowing the virtual abutment $8d$ to have a 3D movement such that 3D coordinates of another end side engagement surface of the virtual abutment $8d$ overlap 3D coordinates of one end side engagement surface of the virtual fixture $7d$. In this case, the 3D movement should be understood as a concept encompassing substantially moving a 3D appearance information image corresponding to a real object in the 3D work image ($1d$) and recalculating the 3D coordinates.

In detail, the one end of the fixture is formed with the polygonal fastening groove, and the other end of the abutment is formed with a protrusion-shaped engaging fastening portion to be engaged with the fastening groove. Accordingly, it should be understood that the one end side engagement surface of the virtual fixture $7d$ is a recessed surface corresponding to the fastening groove, and the other end side engagement surface of the virtual abutment $8d$ is a protruding surface corresponding to the engaging fastening portion.

In this case, the 3D positions of the virtual abutment $8d$ and the virtual support cylinder $9d$ are adjusted such that 3D coordinates of the recessed surface and 3D coordinates of the protruding surface overlap and match each other. Accordingly, the position in which the virtual abutment $8d$ and the virtual support cylinder $9d$ are virtually arranged may exactly correspond to the position of the abutment and the support cylinder actually implanted in the target dental arch, and the virtual binding hole 501*d* may be designed more precisely.

When the virtual binding hole 501*d* is primarily or preliminarily set on the 3D work image 1*d*, the temporary denture, in which the binding hole corresponding to the virtual binding hole 501*d* is aligned and arranged, is prepared (220 in FIG. 1).

Here, the term "temporary denture" should be understood as a meaning encompassing adhesive false teeth in which a binding hole is perforated, and an artificial teeth portion and an artificial gum portion integrally manufactured through 3D printing and the like and formed with a binding hole formed in advance or perforated later.

In addition, the denture hole guider should be understood as a device for guiding drilling of a binding hole formed to fix the support cylinder to the temporary denture. A denture hole guider manufacturing method includes acquiring the 3D work image, setting the virtual binding hole, and designing and manufacturing the denture hole guider. On the other hand, the false teeth described below should be understood as adhesive type false teeth.

Hereinafter, an example of manufacturing the denture hole guider and drilling the binding hole in the false teeth to process the temporary denture will be described first, and then an example of manufacturing a temporary denture incorporating a binding hole through 3D printing will be described.

In detail, referring to FIGS. 5 and 6, when the virtual binding hole 501*d* is primarily or preliminarily set, an outer surface profile of the denture hole guider is set corresponding to an inner surface-side engagement groove of the basic false teeth image 5*d*. Then, a virtual alignment hole 401*d* aligned while overlapping an extension region of the virtual binding hole 501*d* is set.

In this case, it should be understood that the inner surface-side engagement groove profile of the basic false teeth image 5*d* corresponds to the basic target dental arch image 2*d* displayed on the 3D work image 1*d*. In addition, the basic target dental arch image 2*d* may be displayed by being replaced with an image acquired on the basis of a surface shape of an actual target dental arch or an inner surface-side profile of an engagement groove of the false teeth. Accordingly, when the outer surface profile of the denture hole guider is set along the surface profile of the basic target dental arch image 2*d*, the outer surface profile of the denture hole guider may be set to correspond to the engagement groove profile of the false teeth.

In this case, the virtual alignment hole 401*d* should be understood as design information of an alignment hole formed in the denture hole guider, which is manufactured as a real object, that is, a 3D image or 3D vector data in the 3D work image 1*d*. In addition, the alignment hole should be understood as a perforated portion actually formed in the denture hole guider.

On the other hand, when an inner surface profile is set in consideration of a predetermined support thickness from the outer surface profile of the denture hole guider, solid 3D area information between the outer surface profile and the inner surface profile may be set as body information of the denture hole guider. Here, the body information of the denture hole guider should be understood as primary design information for setting the outer surface profile of the denture hole guider as an external appearance corresponding to the gum surface profile of the target dental arch or the inner surface profile of the engagement groove.

In addition, a virtual denture hole guider 400*d* is set according to the body information of the denture hole guider and is virtually arranged in the 3D work image 1*d*. In this case, the virtual denture hole guider 400*d* should be understood as a meaning encompassing 3D vector data representing the body information or a 3D image corresponding to the vector data. In addition, the virtual arrangement of the virtual denture hole guider 400*d* should be understood as a concept encompassing allowing the body information of the denture hole guider to be displayed in the form of an image in the 3D work image 1*d* or to be calculated as 3D coordinates corresponding to the body information of the denture hole guider.

In detail, the virtual denture hole guider 400*d* is virtually disposed in the 3D work image 1*d* such that the outer surface profile of the virtual denture hole guider 400*d* matches the surface profile of the basic target dental arch image 2*d* or the 3D surface information of the inner surface-side engagement groove of the basic false teeth image 5*d*. In addition, a region of the virtual denture hole guider 400*d* overlapping an extension region of the virtual binding hole 501*d* arranged in the arrangement direction of the virtual support cylinder 9*d* is set as the virtual alignment hole 401*d*. In this case, the set virtual binding hole 501*d* extends in an arrangement direction of the virtual support cylinder 9*d* so as to pass through the virtual denture hole guider 400*d* that is virtually arranged.

In addition, referring to FIGS. 6 and 7B, the body information and region information of the virtual alignment hole 401*d* are matched with each other and are set as design information of the denture hole guider. In addition, the design information of the denture hole guider is transmitted to a manufacturing apparatus 30 (see FIG. 2) such as a 3D printer or a cutting processing device to manufacture the physical denture hole guider 400.

In this case, the denture hole guider 400 is engaged, arranged, and disposed in an engagement groove 502 of the false teeth 5, and the drilling position and angle are guided through the alignment hole 401 formed in the denture hole guider 400 so that the binding hole 501 may be formed in the false teeth 5.

In detail, an opposing engagement portion 402 corresponding to the gum surface profile of the target dental arch protrudes from one surface of the denture hole guider 400 corresponding to the engagement groove 502 of the false teeth 5. The alignment hole 401 is formed to pass through between the other surface portion and one surface portion of the denture hole guider 400 so as to correspond to the virtual binding hole 501*d* preliminarily set in the 3D work image 1*d*.

Accordingly, when the opposing engagement portion 402 is closely engaged to the engagement groove 502, the alignment hole 401 is arranged to correspond to a position continuously arranged with the virtual binding hole 501*d* primary or preliminary set in the 3D work image 1*d*. In addition, when drilling is guided along the alignment hole 401, the binding hole 501 may be precisely processed at the correct position and angle in the false teeth 5. With such a configuration, the false teeth 5 may be simply converted into a temporary denture that may be coupled to a fixture/abutment using the binding hole 501 and the support cylinder.

Further, when designing the denture hole guider 400, an operation of setting a virtual locking portion 403*d* corresponding to an edge of the basic false teeth image 5*d* on the surface of the virtual denture hole guider 400*d* virtually disposed in the 3D work image 1*d* may be included. The virtual locking portion 403d refers to design information for forming a locking portion 403 in the denture hole guider 400, that is, 3D image or 3D vector data set in the 3D work image 1d.

In this case, the virtual locking portion 403d is set to protrude to be engaged with an edge end of the basic false teeth image 5d in a state in which the surface profile of the virtual denture hole guider 400d is disposed to be arranged with the surface profile of the basic target dental arch image 2d. In addition, the virtual locking portion 403d, the body information of the denture hole guider, the virtual alignment hole 401d, and the like may be collected and used as design information of the denture hole guider 400.

Accordingly, the locking portion 403 supporting the edge of the false teeth 5 may be integrally formed along the edge of the opposing engagement portion 402 in the denture hole guider 400. Accordingly, when the denture hole guider 400 is coupled to the false teeth 5, the edge 503 of the false teeth 5 is engaged with and supported by the locking portion 403 so that a close coupling between the engagement groove 502 and the opposing engagement portion 402 is induced. With such a configuration, the alignment hole 401 may be guided and arranged to a position corresponding to the virtual binding hole 501d, thereby improving the machining convenience and precision for the binding hole 501 which is actually perforated in the false teeth 5.

On the other hand, the temporary denture may be manufactured through 3D printing.

In detail, design information of the temporary denture may be primarily acquired on the basis of the surface profile of the target dental arch and the occlusion information displayed on the 3D work image.

In this case, an inner surface profile of the artificial gum portion may be set along a gum surface profile of the basic target dental arch image 2d displayed on the 3D work image 1d. When an outer surface profile is set in consideration of a predetermined support thickness from the inner surface profile of the artificial gum portion, solid 3D area information between the outer surface profile and the inner surface profile may be set as design information corresponding to the artificial gum portion.

In addition, design information of the artificial teeth portion may be set according to the distance between the surface of the artificial gum portion and a mastication surface of the opposing dental arch. In this case, the basic opposing dental arch image 3d displayed on the 3D work image 1d is acquired in a state in which the false teeth mounted on the target dental arch are occluded with the opposing dental arch with an occlusal vertical dimension suitable for the denture subject. Accordingly, the artificial teeth portion may be set to a height that provides a stable mastication sensation through the occlusal vertical dimension. When the primary design information of the temporary denture is transmitted to the manufacturing apparatus 30 (see FIG. 2), such as a 3D printer, the temporary denture in which the artificial gum portion and the artificial teeth portion are integrally formed with each other may be manufactured. In the temporary denture, the binding hole 501 may be perforated using the denture hole guider 400.

Furthermore, a virtual temporary denture set on the basis of the primary design information of the temporary denture may be virtually arranged in the 3D work image. In this case, the virtual temporary denture may be virtually disposed such that an inner surface-side engagement groove matches the gum surface profile of the basic target dental arch image. As the virtual binding hole is matched with and added to the primary design information of the temporary denture to correspond to an overlapping area between the virtual temporary denture and the virtual support cylinder, final design information of the temporary denture may be acquired. Subsequently, when the final design information of the temporary denture is transmitted to the 3D printer, the temporary denture incorporating the binding hole may be manufactured.

Figure 8:
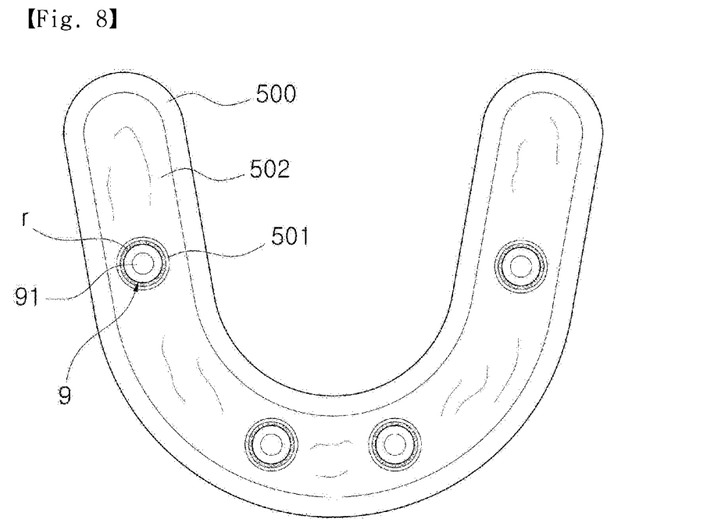
FIG. 8 is a bottom view illustrating a temporary denture in which a binding hole is corrected through a digital denture manufacturing method according to an embodiment of the present invention.
Figure 9A:
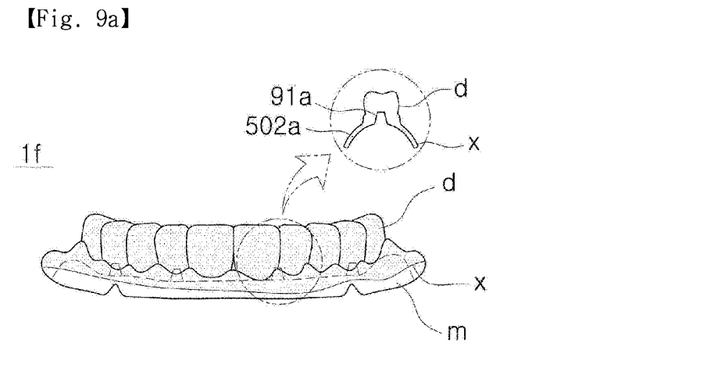
FIGS. 9A and 9B are exemplary diagrams illustrating a process of acquiring a correction surface image in a digital denture manufacturing method according to an embodiment of the present invention.
Figure 9B:
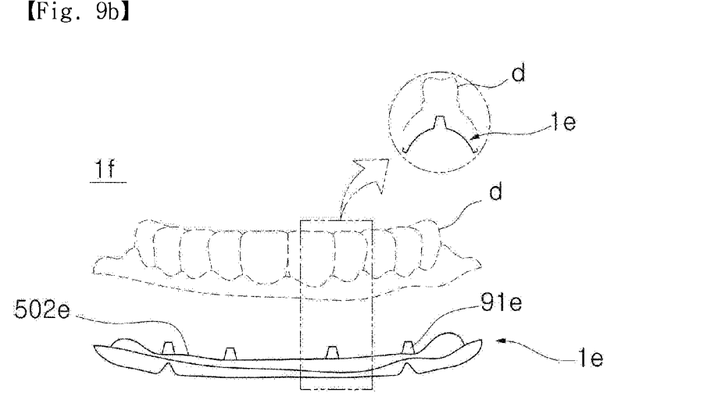
Figure 10A:
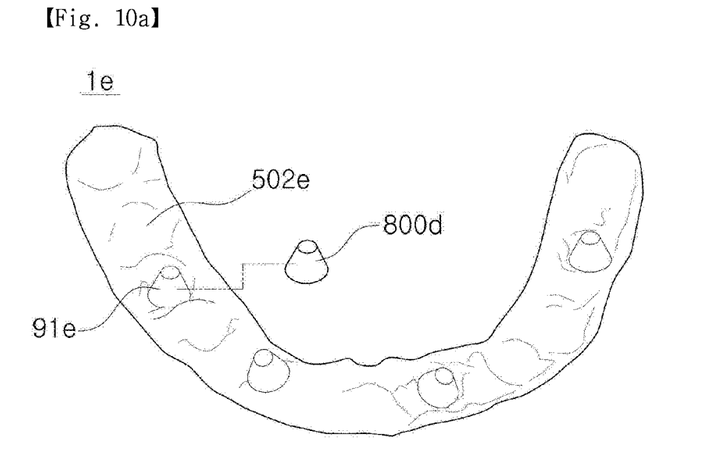
FIGS. 10A and 10B are exemplary diagrams illustrating a process of designing a digital denture through a correction surface image in a digital denture manufacturing method according to an embodiment of the present invention.
Figure 10B:
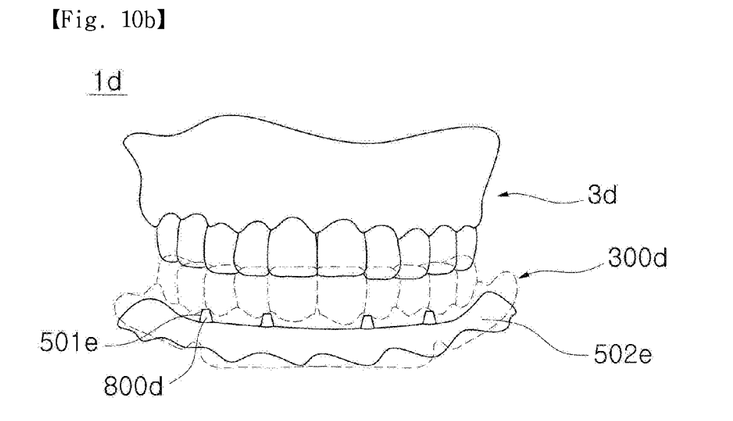
Figure 11:
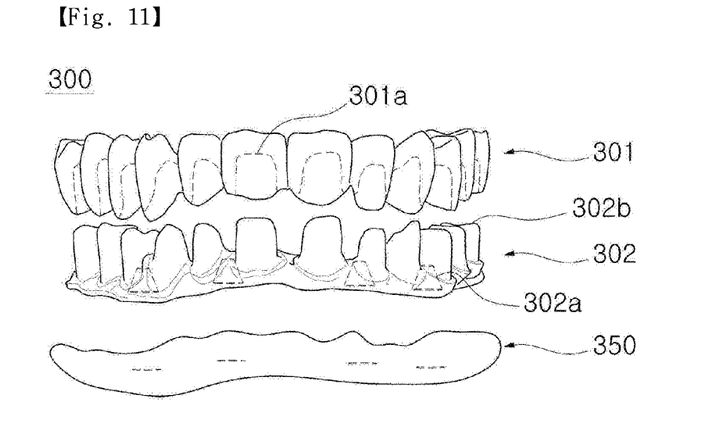
FIG. 11 is an exploded perspective view illustrating a digital denture manufactured by a digital denture manufacturing method according to an embodiment of the present invention.

Meanwhile, FIG. 8 is a bottom view illustrating a temporary denture in which a binding hole is corrected through a digital denture manufacturing method according to an embodiment of the present invention, FIGS. 9A and 9B are exemplary diagrams illustrating a process of acquiring a correction surface image in a digital denture manufacturing method according to an embodiment of the present invention, FIGS. 10A and 10B are exemplary diagrams illustrating a digital denture manufacturing method through a correction surface image in a digital denture manufacturing method according to an embodiment of the present invention, and FIG. 11 is an exploded perspective view illustrating a digital denture manufactured by a digital denture manufacturing method according to an embodiment of the present invention.

Here, a process of manufacturing a final digital denture using a temporary denture 500 corrected to have a correct position is described.

Referring to FIG. 8, the support cylinder 9 is arranged with and coupled to the binding hole 501 of the temporary denture 500. Then, when the support cylinder 9 coupled to the binding hole 501 is coupled to an abutment fastened to a fixture previously implanted in the target dental arch, the temporary denture 500 may be installed in the target dental arch. Accordingly, the temporary denture 500 may be used during the manufacturing period of the final digital denture so that consistent mastication ability may be secured without damaging the appearance, thereby minimizing inconvenience to daily life.

In this case, the binding hole 501 is corrected according to the positional deviation between the fixture previously implanted at a substantial installation position of the temporary denture 500 in the target dental arch and the support cylinder 9 fixed to the temporary denture 500. A lower end portion of the support cylinder 9 fixed to the binding hole 501 that is corrected to the correct position as such is used as a binding region. Here, the binding region includes a binding portion of the abutment fastened to the fixture and should be understood as a region exposed to the outside of the gum.

In detail, the virtual binding hole 501d (see FIG. 6) set in the 3D work image 1d (see FIG. 6) is preliminarily set by including a predetermined tolerance area. Accordingly, the binding hole 501 formed in the temporary denture 500 also has a predetermined tolerance area corresponding to the virtual binding hole 501d (see FIG. 6).

In addition, in a state in which the engagement groove 502 of the temporary denture 500 is engaged with the gum of the target dental arch, an auxiliary processing material r may fill a space between the binding hole 501 and the support cylinder 9. Here, the auxiliary processing material r is provided as a resin or the like and performs a correction process on the binding hole 501. Accordingly, a binding end portion of the support cylinder 9 may be accurately aligned to correspond to the position of the abutment fastened to the fixture implanted in the target dental arch. The binding end portion of the support cylinder 9 may be used as a binding region for precise resetting of the virtual binding groove included in the digital denture design information in a subsequent process of the digital denture manufacturing method.

In the temporary denture, even when the inner circumferential surface of the binding hole is coated only with a resin, the lower end of the binding hole may be used as the binding region. That is, the binding region may be arrangedon the basis of the implant information including the implant position of the fixture and the shape and position of the abutment fastened to the fixture.

On the other hand, one end of the abutment is formed with a binding portion, which is a conical projection, and the binding end portion of the support cylinder 9 is formed with an opposing binding groove 91 corresponding to or engaged with the binding portion. In addition, an auxiliary scan image is acquired along the inner surface-side engagement groove 502 of the temporary denture 500 to which the support cylinder 9 having the opposing binding groove 91 is fixed (230 of FIG. 1).

In detail, referring to FIG. 9A, an auxiliary scan image if is acquired by scanning the entire outer surface of the temporary denture through an intraoral scanner and includes an engagement groove image 502a of inner surface-sides of the artificial teeth portion and the artificial gum portion. In this case, an opposing binding groove image 91a is concavely displayed in the engagement groove image 502a.

Here, the opposing binding groove image 91a is used as a binding region serving as a reference for setting the position and shape of the virtual binding groove for manufacturing the final digital denture. That is, the binding region may be formed to correspond to the outer surface profile of the abutment fastened to the fixture.

In addition, the auxiliary scan image if may be acquired through the temporary denture that has been separated from the target dental arch and may be acquired to display the overall 3D surface shape of the artificial teeth portion and the artificial gum portion.

Meanwhile, from the auxiliary scan image 1f, a correction surface image 1e on 3D surface information of the inner surface-side engagement groove of the temporary denture including the binding region is acquired (240 in FIG. 1). The correction surface image 1e is acquired through the planning unit 20 (see FIG. 2).

In detail, the 3D surface information of the temporary denture included in the auxiliary scan image if is stored by interconnecting a plurality of points having a predetermined coordinate value corresponding to outer surface information of the temporary denture. For example, the 3D surface information of the temporary denture may be stored as a stereolithography (STL) file and may be set to have a triangular face by a plurality of points and lines connecting the points according to an outer shape of the temporary denture. Accordingly, the auxiliary scan image if may be stored as a 3D surface model in which the inside of the outer shape of the temporary denture is substantially hollow.

Furthermore, referring to FIGS. 9A and 9B, the 3D surface information of the temporary denture includes 3D surface information of the artificial teeth portion, which is displayed to have a surface thereof substantially convex upward, and the artificial gum portion, which is displayed to cover a lower end portion of the artificial teeth portion. In addition, the 3D surface information of the temporary denture includes the engagement groove image 502a and the opposing binding groove image 91a which are concavely displayed at the inner surface-side of the artificial gum portion.

In this case, an engagement region portion m is set on the basis of a boundary region x selected and input along an outer edge of the engagement groove image 502a in the 3D surface information of the temporary denture. Here, the outer edge of the engagement groove image 502a should be understood as a boundary line between the engagement groove image 502a and an outer surface portion of the artificial gum portion. In addition, the engagement region portion m includes 3D surface information of the engagement groove image 502a and the opposing binding groove image 91a, that is, 3D surface information of the binding region.

In addition, the 3D surface information of the temporary denture except for the engagement region portion m, that is, the outer surface profile of the artificial gum portion and the artificial teeth portion region, are set to be a deleting region d and deleted. With such a configuration, inner surface-side surface information of the engagement region portion m including the binding region may be exposed to the outside and acquired as the correction surface image 1e.

In this case, since the 3D surface information of the temporary denture is stored as surface information having substantially no thickness, the coordinate values of the inner surface-side profile of the engagement region portion m and the coordinate values of the outer surface-side profile of the engagement region portion m are the same. Accordingly, the correction surface image 1e may be acquired with respect to the 3D surface information of the engagement groove image 502e and the binding region image 91e that are exposed by deleting of the deleting region d. Here, the 3D surface information of the exposed binding region image 91e should be understood as corresponding to 3D surface information of an image of the opposing binding groove whose inner surface-side is exposed to the outside.

That is, the present invention may acquire 3D surface information of the engagement groove and the binding region by a simple method of deleting unrequired parts from an image acquired by scanning the temporary denture. Thus, design information precisely corresponding to the target dental arch and the binding region may be clearly exposed and acquired. In this case, 3D surface information of the engagement groove and the binding region is substantially matched with the appearance profile of the target dental arch and the abutment implanted in the target dental arch so that the digital denture designed and manufactured on the basis of the 3D surface information of the engagement groove and the binding region may have an installation precision that is significantly improved.

Meanwhile, referring to FIGS. 10A and 10B, a virtual abutment 800d extracted from the digital library is virtually disposed to replace and correct 3D surface information of the exposed binding region image 91e (240 in FIG. 1).

Here, the digital library refers to a database including digital appearance information corresponding to a plurality of abutments. That is, the digital library stores a plurality of pieces of digital appearance information corresponding to general abutments and multi abutments of various standards. Accordingly, the digital appearance information of the virtual abutment 800d may be extracted from the digital library according to the implant angle of the fixture and the fastening groove shape information of the fixture.

In addition, the digital library may include digital appearance information of the virtual support cylinder in addition to the virtual abutment, and a physical abutment and a physical support cylinder may be easily manufactured using the digital appearance information. In addition, an abutment and a support cylinder previously manufactured according to the digital appearance information included in the digital library may be immediately used without a separate manufacturing process corresponding to the virtual abutment and the virtual support cylinder.

Here, a registration reference point may be automatically set or manually input at mutually corresponding portions of the binding portion of the virtual abutment 800*d* and the exposed binding region image 91*e*. The virtual abutment 800*d* is disposed to overlap the exposed binding region image 91*e* such that the registration reference points of the objects overlap each other. Accordingly, the distortion or damage that may occur due to saliva, foreign substance, or a scanning process is eliminated, and the surface shape of the binding portion of the abutment implanted in the target dental arch may be accurately displayed in the 3D work image 1*d*.

Preferably, the surface image matched with the 3D work image 1*d* in advance may be replaced and matched with the correction surface image 1*e* so that the 3D work image 1*d* is reacquired. That is, surface information corresponding to the target dental arch is displayed by being replaced with the 3D surface information of the exposed engagement groove image 502*e*, and surface information corresponding to the binding portion of the abutment is displayed by being replaced with the virtual abutment 800*d*.

Accordingly, the re-acquired 3D work image 1*d* includes the correction surface image 1*e*, which replaces the basic target dental arch image, and the basic opposing dental arch image 3*d* that are arranged with an occlusal vertical dimension suitable for the denture subject. In this case, in the correction surface image 1*e*, 3D surface information of the exposed engagement groove image 502*e* and the virtual abutment 800*d* accurately indicating the position and shape of the binding portion of the abutment in the surface profile of the target dental arch are displayed.

An inner surface profile is set according to the 3D surface information of the exposed engagement groove image 502*e*, and a virtual digital denture 300*d* in which the virtual binding groove 501*e* corresponding to the virtual abutment 800*d* is set and formed is designed and manufactured (250 in FIG. 1).

Although the virtual binding groove 501*e* may be formed on the basis of the 3D surface information of the exposed binding region image 91*e*, the virtual binding groove 501*e* may be set in a more exact form by being replaced with the virtual abutment 800*d*.

In this case, the virtual binding groove 501*e* may be set to a shape that is engaged with the binding portion of the abutment without a separate tolerance area. For example, when a hexagonal or polygonal cutting portion for angular alignment is formed on the outer surface of the binding portion of the abutment, the virtual binding groove 501*e* is also set to have a groove shape to be engaged with the cutting portion.

On the other hand, a through-hole may be formed in an upper portion of the virtual digital denture 300*d* in which the virtual binding groove 501*e* is formed so that a screw for coupling the final digital denture to the abutment is inserted into the through-hole.

Accordingly, the present invention may be designed so that the positional relationship between the fixture actually implanted in the target dental arch, the abutment fastened to the fixture, and the digital denture are accurately calculated. In addition, the virtual binding groove 501*e* is precisely designed to accurately reflect the calculated positional relationship of the digital denture, and the installation position and angle of the digital denture according to the position and angle of the fixture/abutment implanted in the target dental arch may achieve clear matching.

The auxiliary scan image if may be inverted through the planning unit 20 (see FIG. 2) to be acquired as a correction surface image. That is, the inner surface-side engagement groove of the temporary denture including the binding region may be inverted to be acquired as an inversion image in which the engagement groove and the binding region are represented in 3D.

In the correction surface image acquired by the inversion, an inversion image of the engagement groove, in which the engagement groove is represented in 3D, and an inversion image of the binding region may be displayed. Here, the inversion image of the binding region should be understood as a shape of the opposing binding groove that is inverted and represented in 3*d*. In addition, surface information corresponding to the target dental arch may be displayed by being replaced with the inversion image of the engagement groove displayed on the correction surface image, and the inversion image of the binding region may be displayed by being replaced with the virtual abutment.

Furthermore, a correction surface image on 3D surface information of the inner surface-side engagement groove of the temporary denture including the support cylinder may be acquired. In addition, 3D surface information of the binding end portion of the support cylinder may be replaced and corrected by the virtual abutment extracted from the digital library corresponding to the abutment.

On the other hand, an inner surface profile of the artificial gum portion is set to correspond to the 3D surface information of the exposed engagement groove image 502*e* displayed in the 3D work image 1*d*. When an outer surface profile is set in consideration of a predetermined support thickness from the set inner surface profile, solid 3D area information between the outer surface profile and the inner surface profile may be set as design information corresponding to the artificial gum portion.

In addition, design information of the artificial teeth portion, in which the height is set according to the distance between the surface of the artificial gum portion and the mastication surface of the opposing dental arch, may be acquired. In addition, according to primary design information of the digital denture including the artificial gum portion and the artificial teeth portion, the virtual digital denture 300*d* may be set and may be virtually disposed in the 3D work image 1*d*. In this case, the virtual digital denture 300*d* should be understood as a meaning encompassing 3D vector data representing the design information of the digital denture or a 3D image corresponding to the vector data.

Here, the virtual digital denture 300*d* is virtually disposed such that the inner surface profile matches the 3D surface information of the exposed engagement groove image 502*e*. The virtual binding groove 501*e* may be matched with the design information of the virtual digital denture 300*d* along an overlapping area between the virtual digital denture 300*d* and the virtual abutment 800*d*. That is, the pieces of design information corresponding to the artificial gum portion, the artificial teeth portion, and the virtual binding groove 501*e* are aggregated so that final design information of the digital denture may be acquired.

Accordingly, the virtual binding groove 501*e* may be precisely designed by accurately reflecting the position in which the fixture/abutment/support cylinder are substantially implanted in the target dental arch, and the binding groove is accurately formed in the digital denture. Furthermore, since the virtual binding groove 501*e* is set on the basis of the virtual abutment 800*d*, the matching accuracy between the binding groove and the fixture/abutment implanted in the target dental arch may be remarkably improved.

With such a configuration, unlike the conventional technology in which the position of the binding groove is determined through the experience of the operator or the eye measurement, a delay process due to additional correction, such as extended cutting or resin addition of the binding groove, is not needed, thereby enabling a rapid and convenient installation. In addition, damage of the binding groove or separation of the denture due to separation or breakage of the added resin are prevented so that stable installation is achieved, thereby improving installation convenience and durability of the product.

Meanwhile, referring to FIG. 11, the acquired final design information of the digital denture is transmitted to the manufacturing apparatus 30 (see FIG. 2) so that the physical digital denture 300 is manufactured (250 of FIG. 1). Here, the digital denture 300 may be used as a device firmly modified to the gum in place of the conventional false teeth.

In detail, the digital denture 300 includes a denture frame 302 and a crown bridge 301. In addition, the digital denture 300 may be provided at a lower portion with a cover portion 350 formed of, for example, a ceramic material matching with the color of the gum so that the denture frame 302 formed of a metallic material is not visually exposed. Instead of the separate cover portion 350, an extension portion matching with the color of the gum may be formed on the lower portion of the denture frame 302 and may be post-processed.

The denture frame 302 is a portion corresponding to an artificial gum portion and may be formed of a ceramic or metal material having a high strength and biocompatibility. Here, an engagement groove is formed in one surface portion of the denture frame 302, and a plurality of support protrusions 302b, to which the crown bridge 301 is coupled, are formed on the other surface portion of the denture frame 302. In addition, the binding groove 302a is formed in the engagement groove at a position matching with the virtual binding groove 501e.

In addition, the crown bridge 301 is a portion corresponding to the artificial teeth portion and may be formed of a ceramic or metal material having high strength and biocompatibility and is provided on one surface thereof with a support groove portion 301a into the support protrusion 302b is inserted.

In this case, the digital denture 300 may be manufactured by a 3D printer but more preferably may be manufactured by a milling and machining device for high processing precision without limitation of processing materials. Accordingly, an artificial denture having high processing precision and durability may be provided.

As such, unlike the conventional technology of acquiring an actual impression on a fixture implanted in a target dental arch and an impression coping, the present invention may manufacture a digital denture with simple design and high precision using a 3D work image. In addition, since design information of the digital denture is simply stored and managed by 3D vector data, remanufacturing is easily performed using the stored design information of the digital denture when the denture is damaged or lost so that the manufacturing convenience may be improved.

Furthermore, the virtual binding hole is set with a very high precision by virtually arranging the virtual support cylinder on the basis of the image of the support cylinder, the fixed position of which is corrected through a substantial installation process of the temporary denture. Thus, a digital denture having a binding groove fixed at a substantial implant position of the fixture/abutment may be manufactured.

Although the exemplary embodiments of the present invention have been described in the specification and the accompanying drawings, the exemplary embodiments are intended to not limit the technical spirit of the present invention, and those skilled in the art should appreciate that various substitutions, modifications, and changes are possible without departing from the scope and spirit of the present invention.

INDUSTRIAL APPLICABILITY

The present invention is applicable to manufacturing a dental prosthesis.

The invention claimed is:

1. A digital denture manufacturing method comprising the steps of:
   a first step of acquiring a three-dimensional (3D) work image, on which occlusion information between a target dental arch and an opposing dental arch and implant information of a fixture implanted in the target dental arch are displayed, and preparing a temporary denture in which a binding region formed to correspond to a binding portion profile of an abutment fastened to the fixture is arranged;
   a second step of acquiring an auxiliary scan image for the temporary denture;
   a third step of acquiring, from the auxiliary scan image, a correction surface image on 3D surface information of an inner surface-side engagement groove of the temporary denture including the binding region; and
   a fourth step of designing and manufacturing a digital denture having a virtual binding groove corresponding to a position and shape of the 3D surface information of the binding region in an inner surface profile set according to the 3D surface information of the engagement groove,
   wherein the third step further includes:
   virtually arranging a virtual abutment extracted from a digital library corresponding to the abutment to correspond to the 3D surface information of the binding region included in the correction surface image; and
   replacing and correcting the 3D surface information of the binding region along an outer periphery region of the virtual abutment,
   wherein the fourth step includes:
   virtually arranging a virtual digital denture in which an artificial gum portion and an artificial teeth portion are set on the basis of the 3D work image that is replaced and matched with the correction surface image; and
   designing the digital denture such that the virtual digital denture is matched with the virtual binding groove to correspond to an overlap region between the virtual digital denture and the virtual abutment.

2. The digital denture manufacturing method of claim 1, wherein the fourth step includes:
   setting an engagement region portion on the basis of a boundary region selectively input along an outer periphery side of the engagement groove in the 3D surface information of the temporary denture included in the auxiliary scan image; and
   deleting the 3D surface information of the temporary denture except for the engagement region portion such that inner surface-side surface information of the engagement region portion including the binding region is exposed and acquired as the correction surface image.

3. The digital denture manufacturing method of claim 2, wherein in the third step, the 3D surface information of the temporary denture is stored by interconnecting a plurality of points having preset coordinate values corresponding to outer surface information of the temporary denture included in the auxiliary scan image.

4. The digital denture manufacturing method of claim 2, wherein in the third step, the correction surface image is acquired as an inversion image in which the inner surface-side engagement groove of the temporary denture including the binding region is inverted and the engagement groove and the binding region are represented in 3D.

5. The digital denture manufacturing method of claim 4, wherein in the third step, a virtual abutment extracted from a digital library corresponding to the abutment is virtually disposed to correspond to the inversion image of the binding region, and the inversion image of the binding region is replaced and corrected along an outer periphery region of the virtual abutment.

6. The digital denture manufacturing method of claim 1, wherein the first step further includes arranging a binding end portion of a support cylinder to correspond to the binding portion profile of the abutment,
wherein in the third step, from the auxiliary scan image, a correction surface image on the 3D surface information of the inner surface-side engagement groove of the temporary denture including the support cylinder is acquired, and
3D surface information of the binding end portion of the support cylinder is replaced and corrected by a virtual abutment extracted from a digital library corresponding to the abutment.

7. A digital denture manufacturing system comprising:
an imaging apparatus configured to acquire a three-dimensional (3D) work image, on which occlusion information between a target dental arch and an opposing dental arch and implant information of a fixture implanted in the target dental arch are shown and an auxiliary scan image for a temporary denture in which a binding region formed to correspond to an abutment fastened to a fixture implanted in a target dental arch is arranged;
a planning unit configured to acquire, from the auxiliary scan image, a correction surface image on three-dimensional (3D) surface information of an inner surface-side engagement groove of the temporary denture including the binding region, set an inner surface profile according to the 3D surface information of the engagement groove, and set a virtual binding groove corresponding to a position and shape of the 3D surface information of the binding region in the inner surface profile so that a digital denture is designed;
a manufacturing apparatus configured to manufacture the designed digital denture; and
a digital library storage including profiles according to types of the abutment,
wherein the planning unit replaces and corrects the 3D surface information of the binding region with a virtual abutment extracted from the digital library and virtually disposed and sets the virtual binding groove corresponding to the virtual abutment so that the digital denture is designed,
wherein the planning unit virtually arranges the virtual abutment extracted from the digital library corresponding to the abutment to correspond to the 3D surface information of the binding region included in the correction surface image and replaces to correct the 3D surface information of the binding region along an outer periphery region of the virtual abutment, and
wherein the planning unit virtually arranges a virtual digital denture in which an artificial gum portion and an artificial teeth portion are set on the basis of the 3D work image that is replaced and matched with the correction surface image and designs the digital denture such that the virtual digital denture is matched with the virtual binding groove to correspond to an overlap region between the virtual digital denture and the virtual abutment.

* * * * *